United States Patent

Karrer et al.

[11] 4,348,524
[45] Sep. 7, 1982

[54] AMIDE DERIVATIVES OF POLYALKYLPIPERIDINES

[75] Inventors: Friedrich Karrer, Zofingen; Paul Moser, Riehen, both of Switzerland

[73] Assignee: Ciba-Geigy Corporation, Ardsley, N.Y.

[21] Appl. No.: 244,551

[22] Filed: Mar. 17, 1981

[30] Foreign Application Priority Data

Mar. 28, 1980 [CH] Switzerland .................. 2493/80

[51] Int. Cl.$^3$ ............................................ C07D 211/58
[52] U.S. Cl. .................................... 546/187; 546/190; 546/208; 546/224; 544/130; 524/99; 524/103
[58] Field of Search .............. 546/187, 190, 208, 224; 544/130

[56] References Cited

U.S. PATENT DOCUMENTS

| | | | |
|---|---|---|---|
| 3,684,765 | 2/1972 | Matsui et al. | 260/45.8 N |
| 3,904,581 | 11/1975 | Murayama et al. | 260/45.8 N |
| 3,907,803 | 4/1975 | Ramey et al. | 260/270 |
| 4,118,368 | 10/1978 | Soma et al. | 546/187 |
| 4,191,653 | 3/1980 | Brunetti et al. | 546/190 |

Primary Examiner—Robert T. Bond
Attorney, Agent, or Firm—Harry Falber

[57] ABSTRACT

Compounds of the formula I

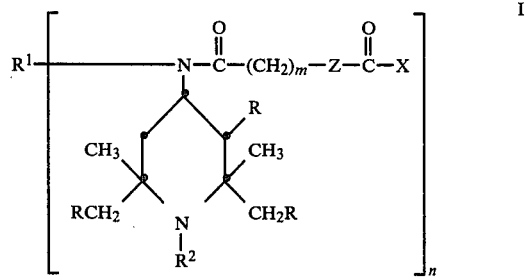

in which m is 0 or 1 and n is 1 or 2 and R, $R^1$, $R^2$, Z and X are as defined in claim 1, and also salts of these compounds, are valuable light stabilizers for organic materials, especially for polymers. The compounds of the formula I can be prepared from the corresponding 4-sec.-aminopiperidines by reaction with cyclic dicarboxylic acid anhydrides and appropriate further reactions.

7 Claims, No Drawings

AMIDE DERIVATIVES OF POLYALKYLPIPERIDINES

The invention relates to novel amide derivatives of polyalkylpiperidines and their use as light stabilisers for organic material, especially for polymers, and also their use as intermediates for the preparation of oligomeric light stabilisers.

It has been disclosed in German Offenlegungsschrift No. 2,040,975 and German Offenlegungsschrift No. 2,349,962 that 4-acylamino-2,2,6,6-tetraalkylpiperidines are valuable light stabilisers for synthetic polymers. However, these compounds have not yet found any industrial use, mainly because their volatility is too high at the temperatures required when processing polymers to impart shape.

In U.S. Pat. No. 3,907,803, 4-acylamino-polyalkyl-piperidines have been proposed in which the acyl radical is derived from a dicarboxylic acid and which have the following formula

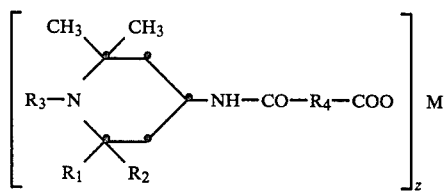

in which M is hydrogen or a monovalent to tetravalent metal cation. Metal salts of this type are not volatile at the processing temperatures for the conventional plastics, but they are not sufficiently compatible with many polymers. This results in a non-uniform distribution in the plastic and also in migration and efflorescence.

Similar compounds have now been found which, however, have better compatibility with polymers and a higher solubility in lacquers.

The invention relates to compounds of the formula

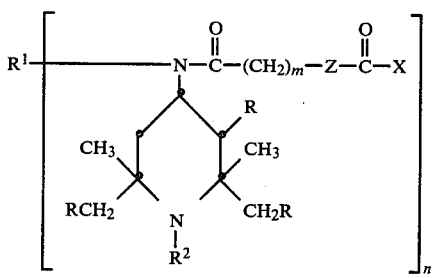

in which m is 0 or 1 and n is 1 or 2, X is —OH, —OR$^3$ or —N(R$^4$)R$^5$), R is hydrogen or CH$_3$, R$^1$, if n is 1, is C$_1$–C$_{18}$-alkyl, C$_2$–C$_4$-hydroxyalkyl, C$_3$–C$_5$-methoxyalkyl, C$_5$–C$_8$-cycloalkyl, C$_6$–C$_7$-cycloalkylmethyl, unsubstituted C$_7$–C$_{12}$-aralkyl or C$_7$–C$_{12}$-aralkyl substituted by C$_1$–C$_4$alkyl and/or hydroxyl, or phenyl, 2-cyanoethyl, 2-alkoxy-(C$_1$–C$_4$)-carbonylethyl or a group of the formula II or III

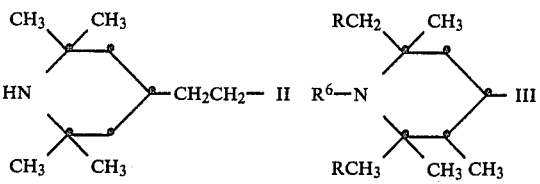

and if n is 2 is C$_2$–C$_{12}$-alkylene, C$_2$–C$_{12}$-alkylene interrupted by one or more —O— or —N(R$^7$)—, or C$_6$–C$_{18}$-cycloalkylene, R$^2$ is hydrogen, an oxyl radical, C$_1$–C$_{12}$-alkyl, C$_2$–C$_4$-hydroxyalkyl, C$_3$–C$_5$-alkenyl, propargyl, benzyl or acetyl, Z is a group

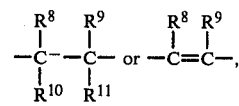

R$^3$ is C$_1$–C$_{12}$-alkyl, C$_2$–C$_4$-hydroxyalkyl, C$_3$–C$_{10}$-alkoxyalkyl, C$_3$–C$_5$-alkenyl, benzyl, cyclohexyl or a radical of the formula III, R$^4$ is hydrogen, C$_1$–C$_{12}$-alkyl, C$_3$–C$_5$-alkenyl, benzyl or cyclohexyl and R$^5$ is hydrogen, C$_1$–C$_{12}$-alkyl, allyl, C$_2$–C$_4$-hydroxyalkyl, cyclohexyl or a radical of the formula III, or R$^4$ and R$^5$ together with the N atom to which they are bonded form a pyrrolidine, piperidine, hexamethyleneimine or morpholine ring, and R$^6$ is hydrogen or methyl, R$^7$ is methyl or an acyl radical —CO—(CH$_2$)$_m$—Z—CO—X, R$^8$ is hydrogen or C$_1$–C$_{18}$-alkyl and R$^9$ is hydrogen, C$_1$–C$_{18}$-alkyl, C$_3$–C$_{12}$-alkenyl or phenyl, or R$^8$ and R$^9$ together with the two carbon atoms to which they are bonded form a saturated or unsaturated, at least 5-membered, carbocyclic ring, and R$^{10}$ and R$^{11}$ independently of one another are hydrogen or methyl, and to salts of these compounds with mineral acids, sulfonic acids or organic phosphoric acids, and also to salts of the compounds of the formula I in which X is —OH with monovalent to trivalent metals.

These compounds differ from the abovementioned compounds of U.S. Pat. No. 3,907,803 in particular in that the nitrogen atom in the 4-position of the piperidine ring does not carry a hydrogen atom.

In the formula I, R$^2$, R$^3$, R$^4$ and R$^5$ can be alkyl having 1–12 C atoms. These radicals can be straight-chain or branched, for example methyl, ethyl, propyl, isopropyl, butyl, tert.-butyl, hexyl, octyl, isooctyl, decyl or dodecyl. R$^1$, R$^8$ and R$^9$ can, in addition, also be higher alkyl radicals, such as tetradecyl, hexadecyl or octadecyl.

R$^2$, R$^3$ and R$^4$ can be C$_3$–C$_5$-alkenyl, for example allyl, crotyl, methallyl or 3-methylbut-2-enyl. As alkenyl having 3–12 C atoms, R$^9$ can, in addition, also be hexenyl, octenyl or dodecenyl.

Cycloalkyl R$^1$ can be, for example, cyclopentyl, cyclohexyl or cyclooctyl. Cycloalkylmethyl R$^1$ can be cyclopentylmethyl or cyclohexylmethyl. As unsubstituted aralkyl or aralkyl substituted by lower alkyl and/or hydroxyl, R$^1$ can, for example, be benzyl, phenylethyl, phenylpropyl, 4-isopropylbenzyl, 3-hydroxybenzyl, 2-methyl-4-tert.-butylbenzyl, 4-hydroxy-3,5-di-tert.-butyl-benzyl or 3-hydroxy-2,6-dimethyl-4-tert.-butylbenzyl. Hydroxy- or methoxy-alkyl R$^1$ can be, for example, 2-hydroxyethyl, 2-hydroxypropyl, 3-hydroxypropyl, 2-hydroxybutyl or 2-methoxyethyl.

If n is 2, $R^1$ can be alkylene, which can be straight-chain or branched and can be interrupted by —O— or —N($R^7$)—. Examples of such radicals are the radicals 1,2-ethylene, 1,2-propylene, 1,3-propylene, tetramethylene, 2,2-dimethyl-1,3-propylene (neopentylene), hexamethylene, 2,2,4-trimethylhexamethylene, octamethylene, dodecamethylene, 4-oxaheptamethylene, 3,6-dioxaoctamethylene, 4-methylaza-heptamethylene, 3,6-di-(methylaza)-octamethylene or 3-methylaza-pentamethylene. An acyl radical $R^7$ is identical to the two acyl radicals on the nitrogen in the 4-position of the piperidine radicals.

Cycloalkylene $R^1$ can be, for example, 1,4-cyclohexylene, 1,3-cyclohexylene, 1,3- or 1,4-bis-(methylene)cyclohexane or dicyclohexylmethane-4,4'-diyl.

$R^8$ and $R^9$ together with the two C atoms to which they are bonded can form a carbocyclic ring. Examples of such rings are a cyclohexane, cyclohexene, endomethylenecyclohexane, endocyclohexene, cyclooctane or 1,2-phenylene ring.

Hydroxyalkyl $R^3$ can be, for example, 2-hydroxyethyl, 2-hydroxypropyl or 2-hydroxybutyl. Alkoxyalkyl $R^3$ can be, for example, 2-methoxyethyl, 2-butoxyethyl, 3-ethoxypropyl or 2-isopropoxybutyl.

The free carboxylic acids of the formula I (X=OH) can be prepared by reacting a 4-amino-polyalkylpiperidine of the formula IV with a cyclic anhydride of a 1,2- or 1,3-dicarboxylic acid of the formula V:

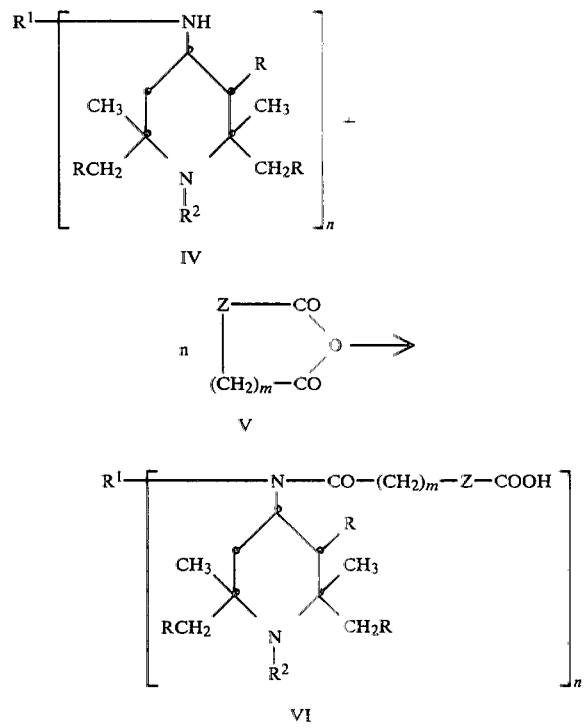

The 4-aminopiperidines of the formula IV are known compounds which in general can be prepared by reductive amination of 4-oxopiperidines with the monoamines $R^1$-$NH_2$ or diamines $H_2N$—$R^1$—$NH_2$. Such compounds are described, for example, in German Offenlegungsschrift No. 2,040,975 and German Offenlegungsschrift No. 2,349,962, and the use of these compounds as light stabilisers is also described in these publications.

The cyclic anhydrides of the formula V are likewise known compounds. Some of them are obtainable commercially. Examples are the anhydrides of succinic acid, citraconic acid and α-alkyl- and α-alkenyl-succinic acids, maleic acid, 2,3-dimethylmaleic acid, cyclohexane-1,2-dicarboxylic acid, phthalic acid, tetrahydrophthalic acid, 2,5-endomethylene-cyclohexane-1,2-dicarboxylic acid, 2,5-endoxotetrahydrophthalic acid, glutaric acid, α-alkylglutaric acid, homophthalic acid or hexahydrohomophthalic acid.

The reaction of IV with the anhydrides of the formula V is preferably carried out in an inert solvent and, if necessary, with warming. Examples of solvents which can be used are benzene, toluene, xylene, dioxane, tetrahydrofuran or dialkyl ethers.

If the cyclic anhydride V which is used is unsymmetrical, there is a possibility that two structural isomers of VI will form. This may be illustrated by taking as an example the use of a monoalkylsuccinic anhydride.

$R^1$—NH +
  |
  Pip

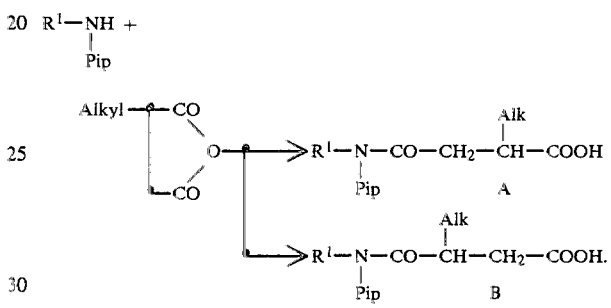

It has been found that in such cases it is in the main the isomer A which is formed, i.e. a mixture of A and B is formed which consists mainly of A. This isomerism is of no significance if the compounds are to be used as stabilisers and it is not necessary to separate the mixture.

The carboxylic acids of the formula VI are in the form of betaines, i.e. inner salts. True acid addition salts can be obtained from these by treatment with strong acids, such as mineral acids, sulfonic acids or organic acids of phosphorus. Examples of such acids are hydrochloric acid, sulfuric acid, phosphoric acid, ethylphosphoric acid, phenylphosphonic acid, methylphosphonic acid, 4-dodecylbenzenesulfonic acid, dinonylnaphthalene-mono- and -di-sulfonic acid or toluenesulfonic acid.

If the compounds of the formula VI contain more than one basic nitrogen atom, it is possible for partial acid addition salts to form.

When the betaines of the formula VI are treated with strong bases, the corresponding metal salts are obtained. Suitable strong bases are, in particular, alkali metal hydroxides and alkali metal alkoxides. By reacting the alkali metal salts, which are thus obtainable, with salts of metals of groups III–VA or IIb–VIII of the periodic table, it is possible to obtain the corresponding salts of the compounds of the formula VI.

The compounds of the formula VI can be converted to the corresponding carboxylic acid chlorides (formula I, X=Cl) by reaction with thionyl chloride, preferably in an inert solvent. These acid chlorides can be converted to the esters of the formula I, in which X is —$OR^3$ by reaction with alcohols of the formula $R^3$—OH. However, it is not necessary, for this purpose, to isolate the acid chlorides. It is also possible to use the acids VI direct as starting materials for the preparation of the esters, by dissolving or suspending these acids in the alcohol R³OH and slowly adding thionyl chloride, in the stoichiometric amount required for VI, to this mixture. Advantageously, the alcohol R³OH will be used in excess for this one-pot reaction.

A second possibility for the preparation of the esters comprises reacting the alkali metal salts with alkyl halides, alkenyl halides or benzyl halides. The alkali metal salts do not have to be isolated for this reaction. The acids VI are reacted with at least the stoichiometric amount of base, for example with NaOH, KOH, K₂CO₃ or LiCO₃, and at least the stoichiometric amount of halide R³Hal is then added. This is advantageously effected in a polar aprotic solvent, for example in acetone, ethyl acetate, methyl ethyl ketone, dimethylformamide, sulfolane, dimethylsulfoxide or 1,2-dimethoxyethane. This process is advantageous if it is desired at the same time also to introduce the substituent R² on the piperidine nitrogen. In this case, a compound of the formula I is obtained in which X is —OR³ and R² and R³ are identical.

A further possibility for the preparation of the esters comprises reacting the alkali metal salts with dialkyl sulfates. The reaction is preferably carried out in the presence of a proton acceptor in an organic solvent, for example in methyl ethyl ketone, cyclohexanone or dioxane, from which the alkali metal sulfate formed can be removed by filtration. The reaction is brought to completion by warming. If the alkali metal salt of a compound of the formula I in which R² is hydrogen is used for this reaction, alkylation of the piperidine nitrogen can be effected at the same time. In this case, thus, an ester is obtained in which R² and R³ are identical.

The amides of the formula I in which X is —N(R⁴)(R⁵) can be obtained from the acid chlorides by reaction with an amine of the formula HN(R⁴)(R⁵). For this reaction, either 2 mols of amine are used per Cl atom, in order to bind the HCl formed, or 1 mol of the amine and 1 mol of an auxiliary base, which serves as a proton acceptor, are used. Bases of this type which can be used are, for example, tertiary amines, alkali metal hydroxides, or alkali metal carbonates. The amidation is advantageously effected in an inert solvent, for example in benzene, toluene, xylene, ligroin, chloroform, methylene chloride, tetrahydrofuran or dioxane.

The amides of the formula I in which X is —NHR⁴ or —NHR⁵ can also be prepared by reacting the esters of the formula I, in which X is —OR³, with a corresponding amine, preferably at elevated temperature.

The substituent R², if this is not hydrogen, can be introduced at various stages of the synthesis of the compounds of the formula I. For example, the introduction of R² can be effected at the stage of the 4-oxopiperidines or at the stage of the compounds of the formula I. In certain cases, the reaction can be carried out simultaneously with the introduction of other substituents, for example simultaneously with the introduction of R³.

The introduction of an alkyl, alkenyl, propargyl, benzyl or acetyl radical as R² is effected by reacting the NH compound with the corresponding halogen compounds R²Hal, for example with butyl bromide, octyl bromide, allyl chloride, propargyl bromide, benzyl chloride or acetyl chloride. Preferably, this reaction is effected in the presence of hydrogen halide acceptors and in an inert solvent such as toluene, acetone, 2-butanone, cyclohexanone, DMSO, sulfolane, xylene or dibutyl ether. An alkyl radical R² can also be introduced by reaction with dialkyl sulfates or alkyl tosylates. A methyl radical R² can also be introduced by reaction with formaldehyde/formic acid. An acetyl radical R² can also be introduced by means of acetic anhydride. A hydroxyalkyl radical R² can be introduced by reaction with alkylene oxides, for example ethylene oxide or propylene oxide. Products in which R² is an oxyl radical can be prepared from the corresponding NH compounds by reaction with an inorganic or organic peracid or with H₂O₂ in the presence of tungsten catalysts.

The way in which these reactions are carried out corresponds to the general methods for the introduction of substituents into secondary amines, but, because of the steric hindrance at the piperidine nitrogen, it is sometimes necessary to use somewhat more severe reaction conditions (time, temperature).

The introduction of an acyl radical R⁷ is effected at the same time as the reaction of IV with a cyclic anhydride. In this case, the starting material used is a compound of the formula IV in which n is 2 and R¹ is an alkylene radical interrupted by —NH—.

Examples of individual compounds of the formula I are the compounds of the formulae given below. In these formulae, the radical

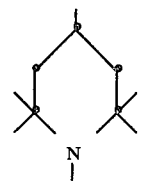

is a 2,2,6,6-tetramethylpiperidine radical.

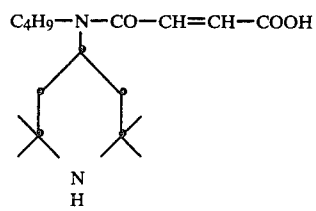

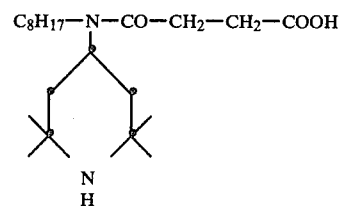

-continued
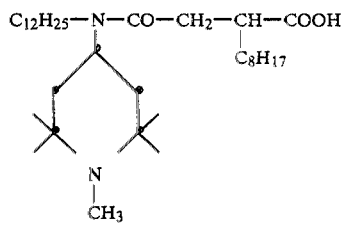
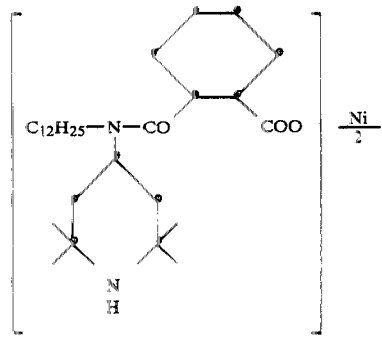
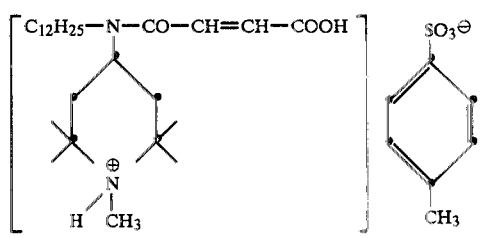
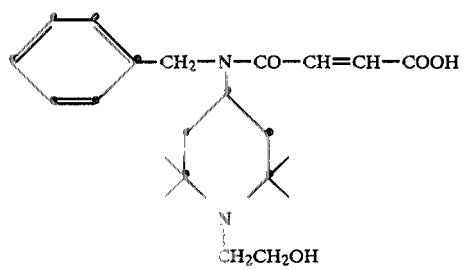
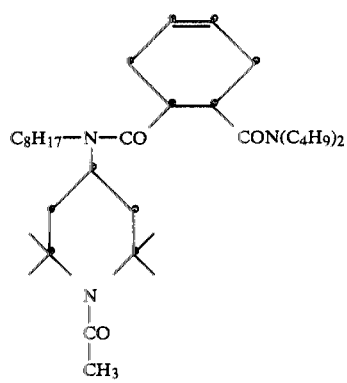
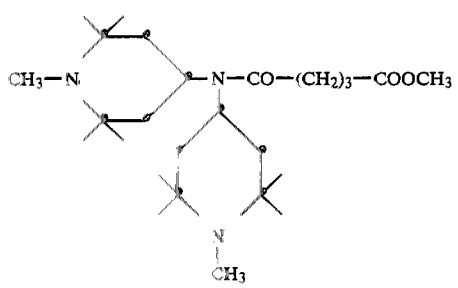
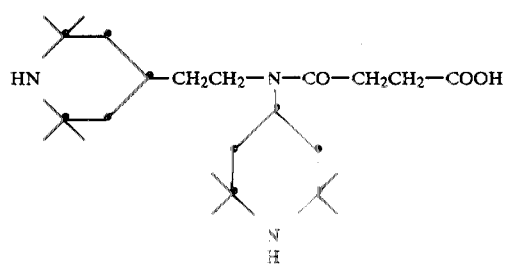
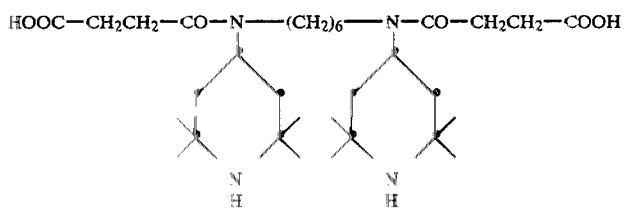
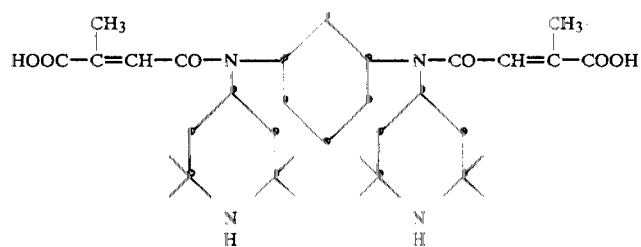

-continued
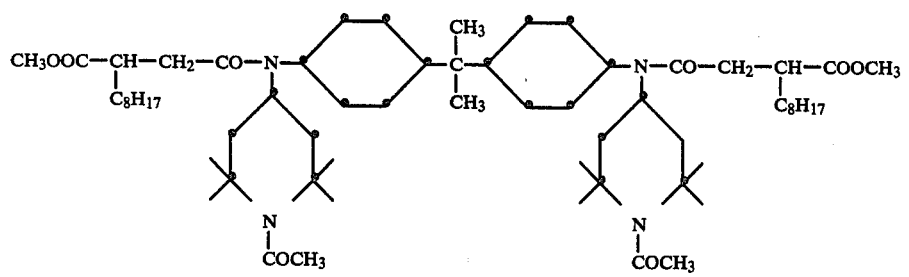
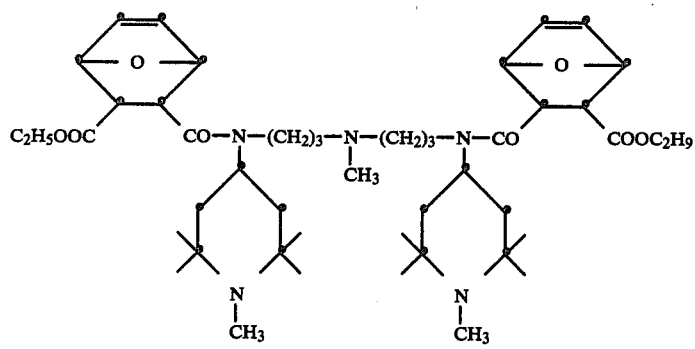
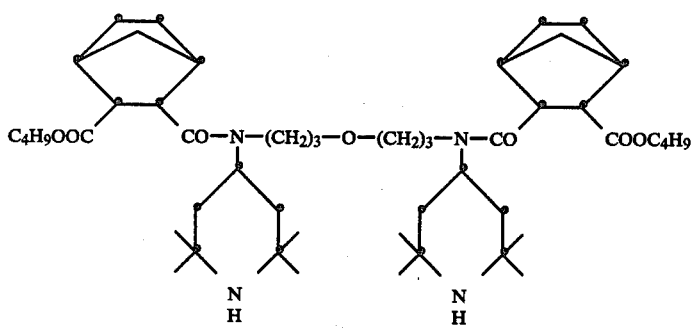
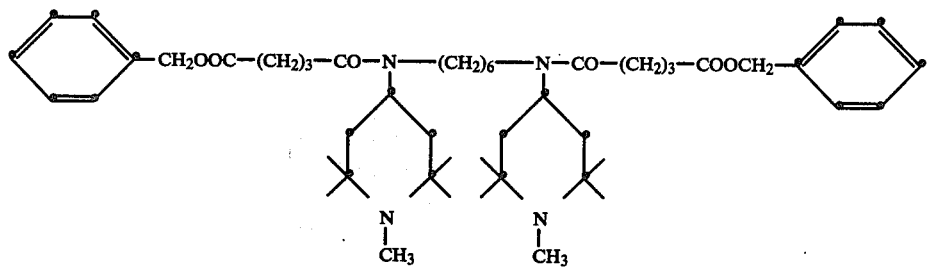
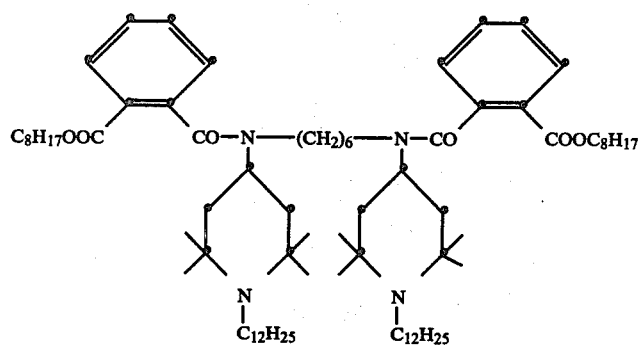

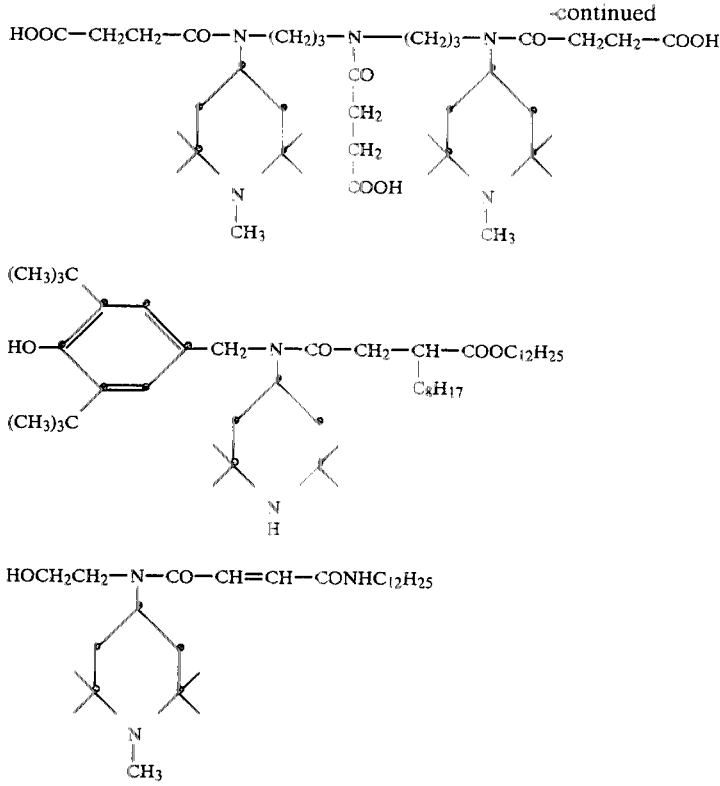

Preferred compounds of the formula I are those in which R is hydrogen.

Further preferred compounds are the compounds of the formula I in which n is 1 and $R^1$ is $C_2$–$C_{12}$-alkyl, and also the compounds of the formula I in which n is 2 and $R^1$ is $C_2$–$C_{12}$-alkylene, or $C_4$–$C_{10}$-alkylene interrupted by —O—.

Further preferred compounds of the formula I are those in which $R^2$ is hydrogen, $C_1$–$C_4$-alkyl, allyl, benzyl or acetyl.

Further preferred compounds of the formula I are those in which m is 0. These are the reaction products of 1,2-dicarboxylic acid anhydrides. Amongst these products of the formula I in which m is 0, preferred compounds are those in which Z is a —CH=CH— or —CH$_2$—CH($R^9$)— group and $R^9$ is hydrogen or alkyl, or in which Z is a 1,2-phenylene, 1,2-cyclohexylene or 1,12,3,6-tetrahydro-1,2-phenylene radical.

Further preferred compounds of the formula I are those in which X is —OH or —$OR^3$ and $R^3$ is alkyl, allyl or benzyl.

The compounds of the formula I are stabilisers for organic materials, in particular to protect them against damage due to the action of light. Materials of this type which have to be protected against the action of light can be oils, fats, waxes, detergents or solvents, but the stabilisers according to the invention are particularly suitable for protecting organic polymers against the action of light. Examples of polymers which can be damaged by the action of light and which can be stabilised by the addition of compounds of the formula I are the polymers listed on pages 22–25 of German Offenlegungsschrift No. 2,805,821.

The stabilisation of polyolefins, styrene polymers, polyurethanes, polyethers, polyesters and polyetheresters is particularly important and the compounds of the formula I are outstandingly suitable for this. Examples of such polymers are high-density polyethylene and low-density polyethylene, polypropylene, ethylene/propylene copolymers, polystyrene, styrene/butadiene/acrylonitrile copolymers, mixtures of polyolefins or of styrene polymers, and polyurethanes based on polyethers or polyesters, in the form of films, fibres, lacquers, elastomers or foams. The use of the compounds of the formula I as light stabilisers for all types of lacquer resins is also of particular importance.

The stabilisers are added to these plastics in a concentration of 0.01 to 5% by weight, based on the material to be stabilised. Preferably, 0.03 to 1.5, and particularly preferentially 0.2 to 0.6, % by weight of the compounds, based on the material to be stabilised, are incorporated into the latter.

Incorporation can be effected after polymerisation, for example by mixing the compounds, and, if desired, further additives, into the melt by the methods customary in the art, before or during shaping, or also by applying the dissolved or dispersed compounds to the polymer, with subsequent evaporation of the solvent if necessary.

The compounds can also be added to the plastics to be stabilised in the form of a master batch which contains these compounds, for example in a concentration of 2.5 to 25% by weight.

In addition to the compounds of the formula I, yet further known stabilisers can also be added to the plastics. These stabilisers can be, for example, antioxidants, light stabilisers or metal deactivators, or also costabilisers, for example those of the phosphorous acid ester type. Furthermore, other additives customary in plastics technology, for example flameproofing agents, antistatic agents, plasticisers, lubricants, blowing agents, pigments, reinforcing materials or fillers, can also be added. Specific examples of such known and conventional additives are listed on pages 25-32 of German Offenlegungsschrift No. 2,349,962.

The invention therefore also relates to plastics which are stabilised by the addition of 0.01 to 5% by weight of a compound of the formula I and which, if desired, can also contain other known and conventional additives. The plastics stabilised in this way can be used in very diverse forms, for example as films, fibres, tapes or profiles, or as binders for lacquers, adhesives or putties.

The compounds of the formula I in which n is 2 and X is —OH or —OR$^3$ can also be used as intermediates for the preparation of oligomeric polyesters or polyamides which have the general formula VII:

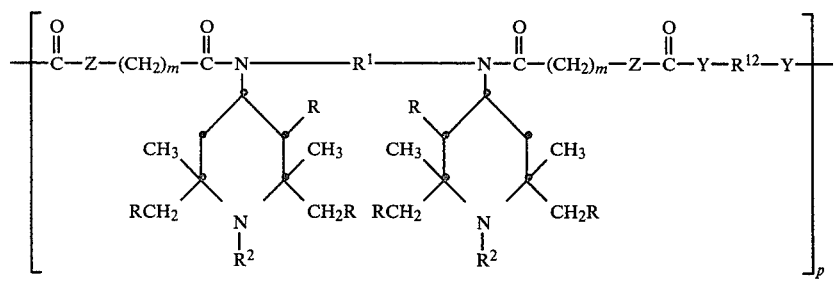

In this formula, m, R, R$^1$, R$^2$ and Z are as defined under formula I, Y is —O— or —NH—, p is a value between 2 and about 50 and R$^{12}$ is a divalent organic radical. Preferably, R$^{12}$ is $C_2$-$C_{20}$-alkylene, or $C_4$-$C_8$-alkylene interrupted by O, or $C_6$-$C_{12}$-arylene, $C_8$-$C_{14}$-aralkylene, $C_6$-$C_{14}$-cycloalkylene, an N,N'-bis-(alkylene)hydantoin, N,N'-bis-(alkylene)-methylene-bis-hydantoin or N,N'-bis-(alkylene)-benzimidazolone radical, a -phenylene-T-phenylene radical, in which T is —$CH_2$—, —$C(CH_3)_2$—, —O—, —S— or —$SO_2$—, or a radical of the formula VIII

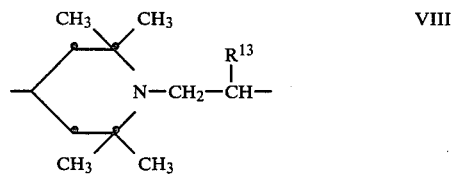

wherein R$^{13}$ is hydrogen, methyl, ethyl, phenyl or phenoxymethyl.

The oligomers of the formula VII are prepared from the compounds of the formula I in which n is 2 and X is —OH or —OR$^3$ by reaction with a diol or a diamine of the formula HY—R$^{12}$—YH. Examples of diols which can be used are aliphatic glycols, such as ethylene glycol, propylene glycol, butane-1,4-diol, neopentylene glycol, diethylene glycol, triethylene glycol, polyethylene glycols, octane-1,8-diol or dodecane-1,12-diol; araliphatic diols, such as p-xylylene glycol or 4,4'-di(hydroxymethyl)-diphenyl; cycloaliphatic diols, such as cyclohexane-1,4-diol or 1,4-di(hydroxymethyl)-cyclohexane; aromatic diols, such as bisphenol A or 4,4'-dihydroxy-diphenyl; or heterocyclic diols, for example 1,3-di-(hydroxyethyl)-5,5-dimethylhydantoin or N,N'-di(hydroxyethyl)-benzimidazolone.

The reaction with the diols results in oligomeric polyesters of the formula VII, in which Y is —O—, and can be carried out by the methods generally known for the preparation of polyesters from dicarboxylic acids or dicarboxylic acid esters and diols. The reaction conditions are so chosen that the degree of polycondensation p of the resulting polyesters is relatively low, in order to ensure good compatibility of the products in plastics. The products of the formula VII which are formed are mixtures of oligomers with different degrees of polycondensation. The value p therefore expresses an average value. Preferably, p is 4 to 20.

The polyamides of the formula VII, in which Y is —NH—, are obtained by reacting the acids or esters I with primary diamines. Examples of suitable diamines are aliphatic diamines such as ethylenediamine, hexamethylenediamine, 4-oxaheptane-1,7-diamine, decamethylenediamine, 2,2,4-trimethylhexamethylenediamine, dodecamethylenediamine, octamethylenediamine or eicosamethylenediamine; cycloaliphatic diamines such as 1,4-diaminocyclohexane, 1,3-bis-(2-aminomethyl)-cyclohexane or 2,2-bis-(4'-aminocyclohexyl)-propane, or aromatic diamines such as 4,4'-diaminodiphenyl, 4,4'-diaminodiphenylmethane or 4,4'-diaminodiphenyl ether.

The reaction is effected by the methods generally known for the formation of polyamides from dicarboxylic acids or dicarboxylic acid esters and diamines. The reaction conditions are so chosen that the average degree of polycondensation p of the resulting polyamides is relatively low, in order to ensure good compatibility of the products in plastics. Preferably, p is 2–12.

The compounds of the formula I in which n is 1, R$^1$ is hydroxyalkyl and X is —OH or —OR$^3$ can be used as intermediates for the preparation of oligomeric polyesters of the formula IX

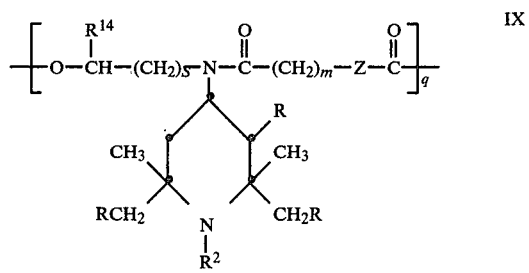

in which R, R$^2$, Z and m are as defined under formula I, s is 1 or 2, R$^{14}$ is H, $CH_3$ or $C_2H_5$ and q has a value of 2–50 and preferably of 4–20. The preparation of these oligomers IX from the carboxylic acids (X=OH) or esters (X=OR$^3$) of the formula I, defined above, is effected by heating in the presence of catalysts. For example, tetraalkyl titanates can be used as the catalyst for the polycondensation of the carboxylic acids. In this case, the reaction is preferably carried out in a solvent which is immiscible with water, and the water which is split off is distilled off from the reaction mixture continuously as an azeotrope. Suitable solvents are, for example, toluene or xylene or deca- or tetra-hydronaphthalene.

Bases, for example LiOH, NaNH₂, potassium tert.-butoxide, Al(O—isoC₃H₇)₃, magnesium oxide or anhydrous zinc acetate or tetraalkyl orthotitanates, can be used as the catalyst for the polycondensation of the esters. In this case, the reaction is preferably carried out without a solvent, the $R^3OH$ which is split off being distilled off.

Oligomeric polyesters and polyamides which contain highly condensed reaction products of diphenols with epichlorohydrin, such as are used as technical grade mixtures for the preparation of epoxide resins. Examples of diglycidyl esters are the diglycidyl esters of succinic acid, adipic acid, sebacic acid, phthalic acid or isophthalic acid.

The compounds of the formula I in which n is 2 and X is —OH and $R^2$ is $C_1$-$C_{12}$-alkyl, $C_3$-$C_5$-alkenyl or benzyl can likewise be reacted with diglycidyl ethers or diglycidyl esters of the formula XI. In this case, the epoxide groups of XI react with the carboxyl groups of I and oligomeric compounds of the formula XII

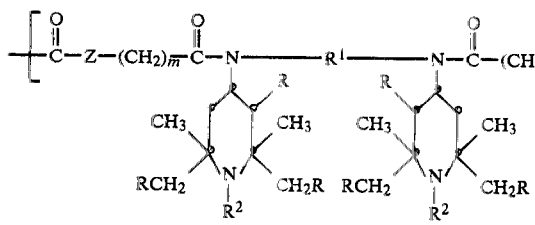

polyalkylpiperidine groups having been disclosed in German Offenlegungsschrift No. 2,719,131, in which their use as light stabilisers for plastics is also described. The oligomeric polyesters and polyamides of the formulae VII and IX can likewise be used as light stabilisers.

The compounds of the formula I in which n is 2 and $R^2$ is hydrogen can also be used as intermediates for the preparation of oligomeric compounds of the formula X:

in which $R^2$ is as defined above and R, $R^1$, Z, E, m and r are as defined under formula X are formed.

The preparation of the oligomers of the formulae X or XII, is effected by warming the two components I and XI in, preferably, an equimolar ratio, i.e. one epoxide group is used per NH group or per COOH group. However, it is also possible to use an excess (about 2-20%) of I or XI if it is intended that the oligomeric compound shall have epoxide end groups. The reaction can be carried out without a solvent or in a polar sol-

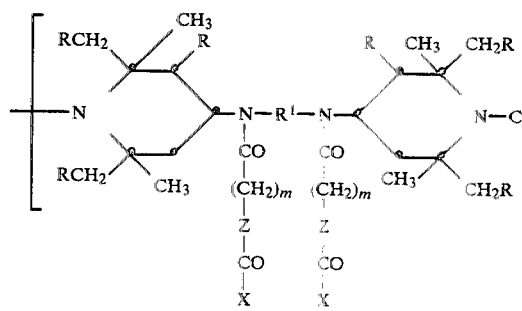

In this formula, R, $R^1$ and Z are as defined under formula I, r has a value between 2 and about 50, preferably 4-12, and E is a divalent, aliphatic, cycloaliphatic or aromatic hydrocarbon radical or dicarboxylic acid radical, especially a $C_2$-$C_{20}$-alkylene radical or the radical of a bisphenol.

These compounds are prepared from the compounds of the formula I in which n is 2 and $R^2$ is hydrogen and X is preferably —$OR^3$ by reaction with a diglycidyl ether or diglycidyl ester of the formula XI

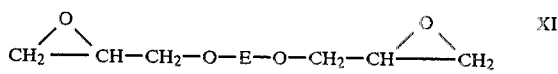

Examples of such diglycidyl ethers are those of ethylene glycol, propylene glycol, butane-1,4-diol, butane-2,3-diol, hexane-1,6-diol, diethylene glycol, 1,4-dihydroxymethyl-cyclohexane, 4,4'-dihydroxydiphenyl, 4,4'-dihydroxydiphenylmethane or bisphenol A (2,2-diphenylolpropane). It is also possible to use more vent. Examples of suitable solvents are, in particular, high-boiling alcohols, glycols and their ethers, for example butanol, butoxyethanol, ethylene glycol or ethylene glycol dimethyl ether. The reaction can be accelerated by the addition of catalytic amounts of tertiary amines or quaternary ammonium salts. Examples of these are tributylamine, benzyldimethylamine, tetramethylammonium chloride or benzyl-trimethylammonium chloride. The reaction conditions should be so chosen that the average degree of polyaddition r of the product is relatively low. Preferably, r has a value of 4 to 12.

The compounds of the formula X and XII are likewise light stabilisers and can be used in the same way as the compounds of the formula I as stabilisers for organic polymers.

The examples which follow describe the preparation of specific compounds of the formula I and their use as light stabilisers and as intermediates for the preparation of oligomers. In these examples, temperatures are in °C. Parts and % are by weight.

EXAMPLE 1

184 g (1.0 mol) of 4-ethylamino-2,2,6,6-tetramethyl-piperidine and 212 g (1.0 mol) of octylsuccinic anhydride are dissolved in 750 ml of xylene and this solution is refluxed for 6 hours. The solvent is distilled off and the brown-yellow resin obtained as the residue is washed cold with acetone. This yields compound No. 1, which has the formula given below, in the form of a beige powder, which is freed from solvent residues at 50° C. and under a pressure of 11 mm Hg. It melts in the temperature range of 125°–139°.

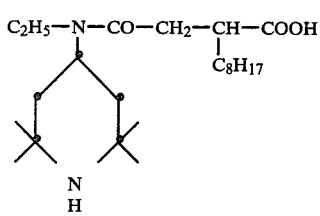

No. 1

EXAMPLE 2

325 g (1.0 mol) of 4-n-dodecylamino-2,2,6,6-tetramethylpiperidine are dissolved in 350 ml of dioxane and this solution is added dropwise in the course of 3 hours at 80° to a solution of 100 g (1.0 mol) of succinic anhydride in 700 ml of dioxane. This reaction mixture is then heated at 80° for 4 hours. On cooling, a precipitate separates out and this is washed with acetone and reprecipitated from dioxane. This yields compound No. 2, which has the formula given below, in the form of a white powder, which is freed from solvent residues at 40° and under a pressure of 100 mm Hg. It melts in a temperature range of 116°–134°.

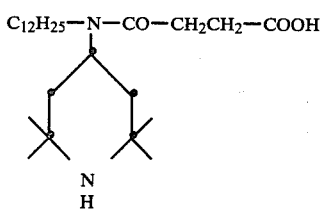

No. 2

The following compounds are prepared analogously:

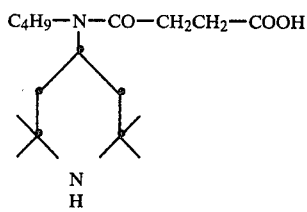

No. 3 melting point 212–217°

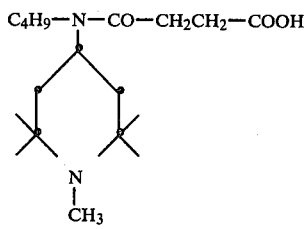

No. 4 softens above 70°.

EXAMPLE 3

325 g (1.0 mol) of 4-n-dodecylamino-2,2,6,6-tetramethylpiperidine and 212 g (1.0 mol) of octylsuccinic anhydride are dissolved in 600 ml of xylene and this solution is then refluxed for 6 hours. On cooling, a precipitate separates out and this is washed with acetone. This yields compound No. 5, which has the formula given below, in the form of a pale beige product, which is freed from solvent residues at 40° and under a pressure of 11 mm Hg. It melts in a temperature range of 100°–107° C.

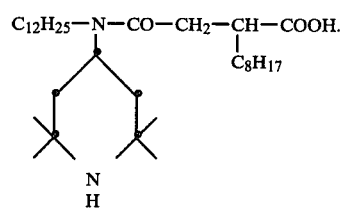

No. 5

EXAMPLE 4

31.6 g (0.08 mol) of 1,6-bis-(2,2,6,6-tetramethyl-4-piperidyl-amino)-hexane, dissolved in 300 ml of toluene, are heated to the reflux temperature and 43 g (0.16 mol) of freshly distilled dodecylsuccinic anhydride are introduced in portions into this solution in the course of one hour. After heating for a further 5 hours, with stirring, the reaction mixture is cooled to about 10°, whereupon compound No. 6 crystallises out. The compound is filtered off, washed well, first with cold toluene and then with hexane, and dried at 60°/0.05 mm Hg. The compound melts in the temperature range of 136°–145°.

$C_{56}H_{106}N_4O_6$ Calculated: C, 72.21, H, 11.47; N, 6.02%. (931.4) Found: C, 72.0, H, 11.4; N, 5.9%.

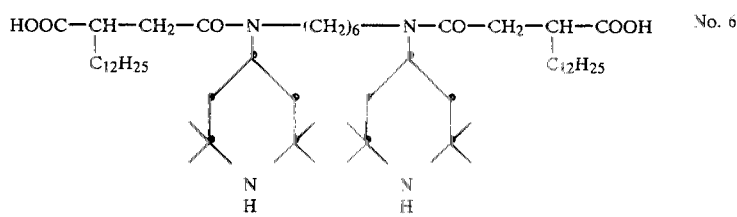

The following compounds are prepared analogously:

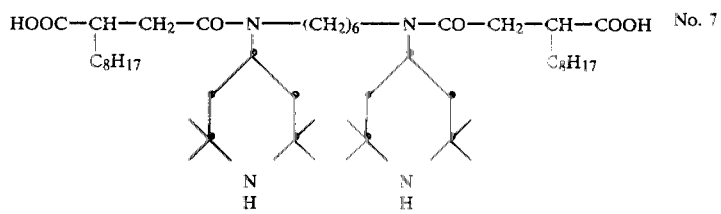

softens above 155°, melts at 188°

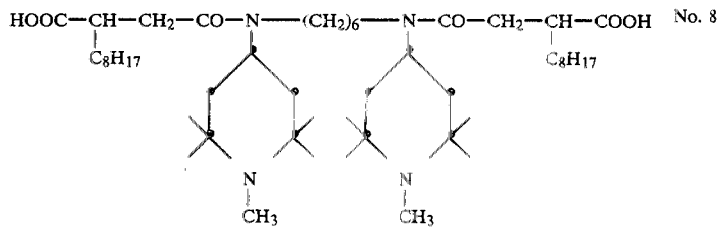

softens above about 70°

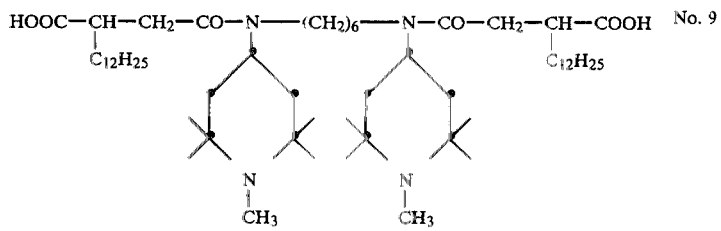

softens above about 85°.

EXAMPLE 5

A solution of 236.8 g (0.6 mol) of 1,6-bis-(2,2,6,6-tetramethyl-4-piperidyl-amino)-hexane is added dropwise in the course of 3 hours, at 60°, to a solution of 120.1 g (1.2 mols) of succinic anhydride in 600 ml of dioxane, with stirring, and the resulting mixture is stirred for a further 20 hours at 60°. It is then cooled to 20° and compound No. 10, which has precipitated, is filtered off, washed with a little dioxane and then with methylene chloride and dried under a high vacuum at 60°. Melting point 278°–282°.

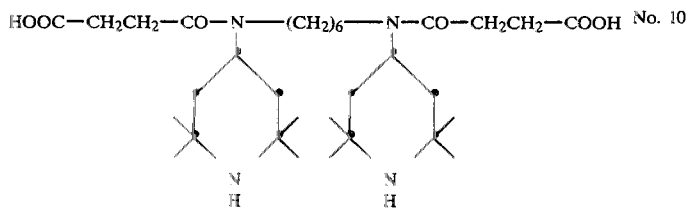

The following compounds are prepared analogously:

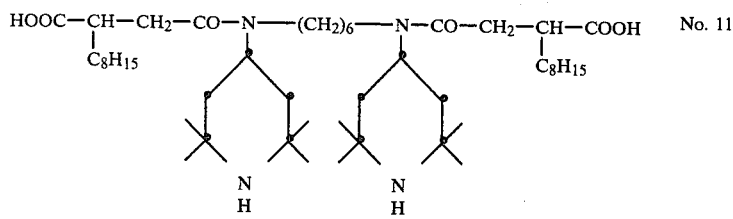
No. 11 softens above 170°, melts at 185°, prepared from technical grade "octenylsuccinic anhydride", position of the double bond not terminated.

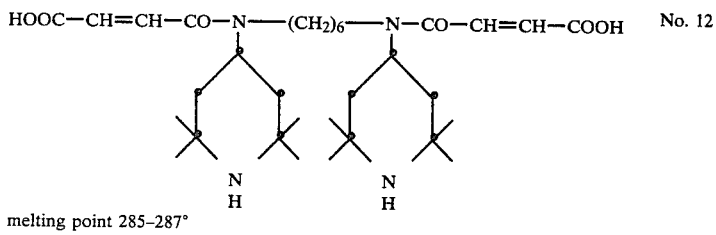
No. 12 melting point 285–287°

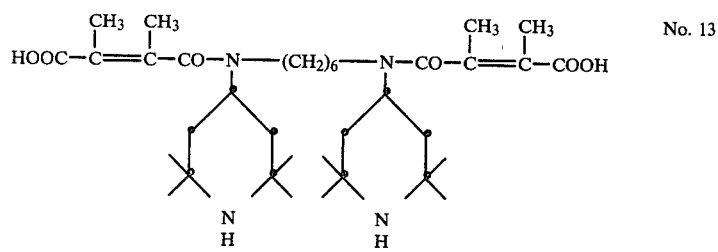
No. 13 mixture of cis and trans isomers, softens above about 160°.

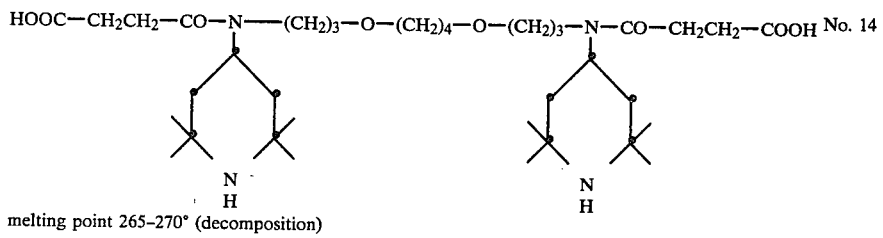
No. 14 melting point 265–270° (decomposition)

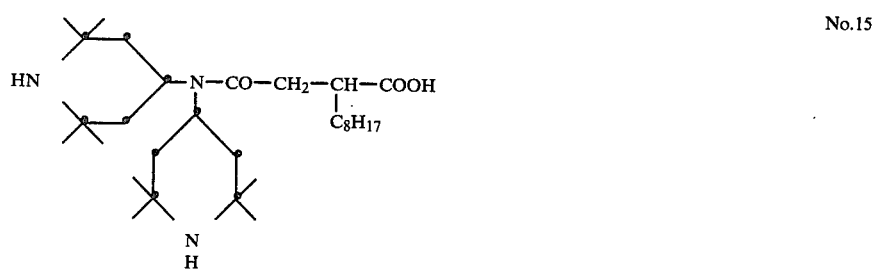
No. 15

If tetrahydrofuran is used as the solvent and the reaction is carried out at 0° to 20°, the following compounds are obtained analogously using the corresponding starting materials:

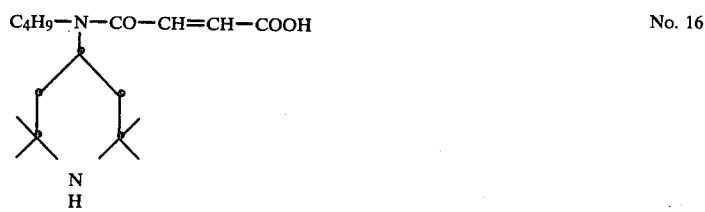
No. 16

-continued
cis isomer, melting point 285–290°
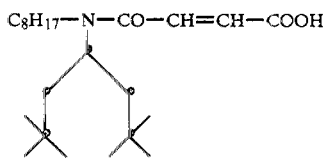   No. 17
cis isomer, melting point 229–232°
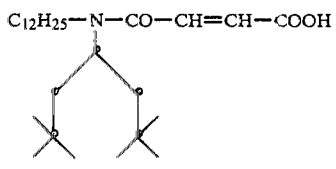   No. 18
cis isomer, softening point about 135°
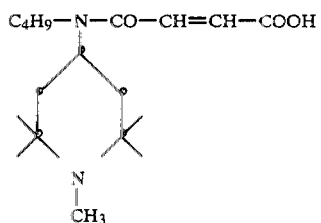   No. 19
cis isomer, melting point 128–135°
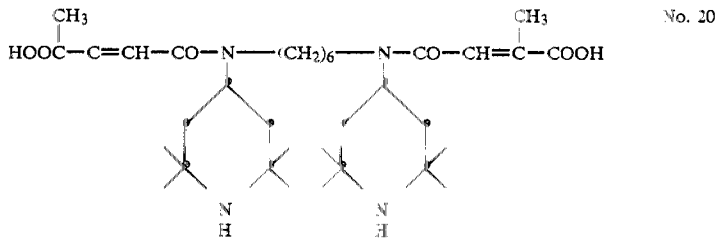   No. 20
melting point 186–188°
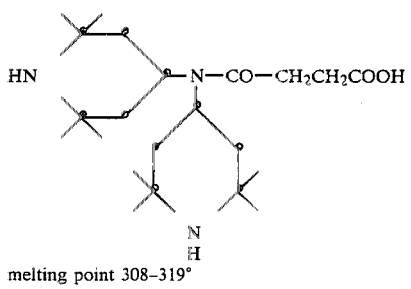   No. 21
melting point 308–319°
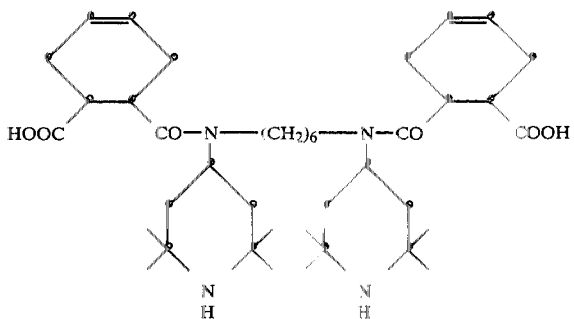   No. 22
melting point 192–195°

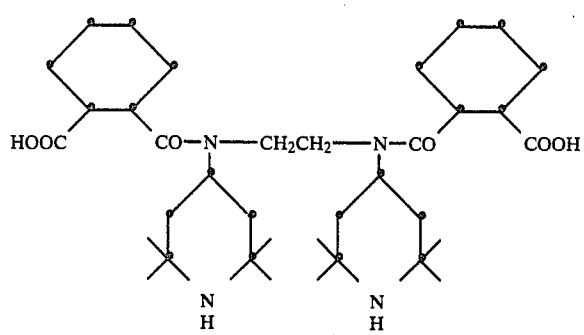

No. 23 mixture of isomers, melting point about 217°

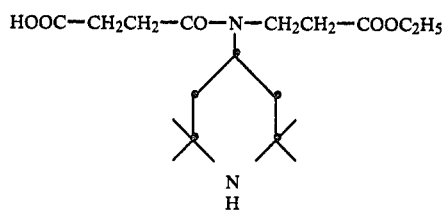

No. 24 melting point 232-233°

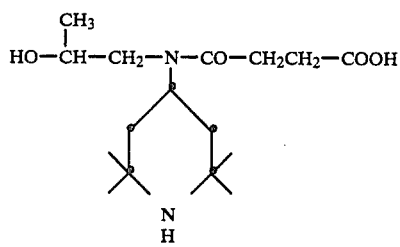

No. 25

(prepared at −20°) melting point 202-205°.

EXAMPLE 6

59.5 g (0.1 mol) of compound No. 10 are suspended in 300 ml of boiling methanol. 25 g (0.21 mol) of freshly distilled thionyl chloride are added dropwise in the course of one hour to this suspension at the reflux temperature, with vigorous stirring, the educt gradually dissolving completely with formation of the dimethyl ester. After stirring under reflux for a total of 22 hours, the pale yellow reaction solution is freed from the solvent in vacuo at about 30°, the residue is dissolved in 500 ml of acetonitrile and this solution is stirred for 3 hours at room temperature with 60 g of finely powdered, solid potassium carbonate. The potassium salts are then filtered off, the filtrate is freed from acetonitrile in vacuo, the residue is dissolved in 500 ml of boiling cyclohexane, the solution is stirred with 5 g of silica gel 60 Merck) the mixture is filtered to give a clear filtrate and compound No. 26 crystallises on cooling and is dried in vacuo. Melting point 120°–121°.

$C_{34}H_{62}N_4O_6$ Calculated: C, 65.56; H, 10.03; N, 9.00%. (622.9) Found: C, 65.8; H, 10.2; N, 8.9%.

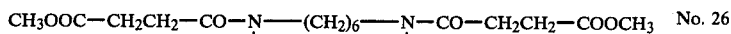
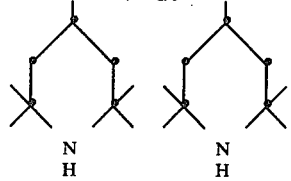

No. 26

The methyl esters No. 27 to No. 31 are obtained analogously from compounds Nos. 14, 7, 21 and 22 and No. 3.

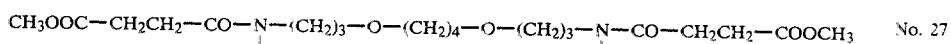
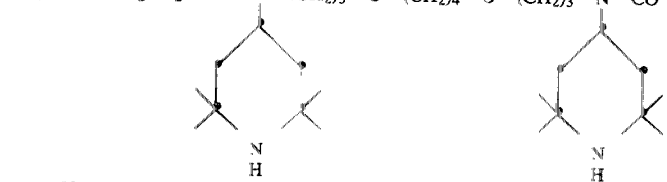 No. 27 oil, $n_D^{25}$ 1.4931

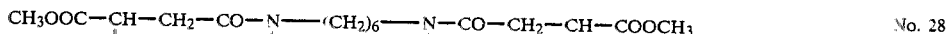 No. 28
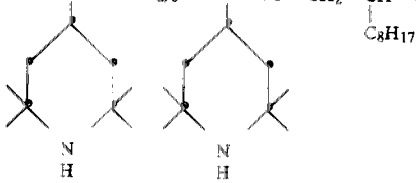

melting point 45–51°.

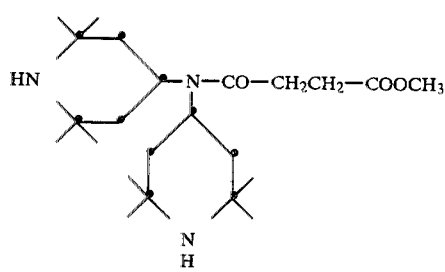 No. 29 melting point 98°

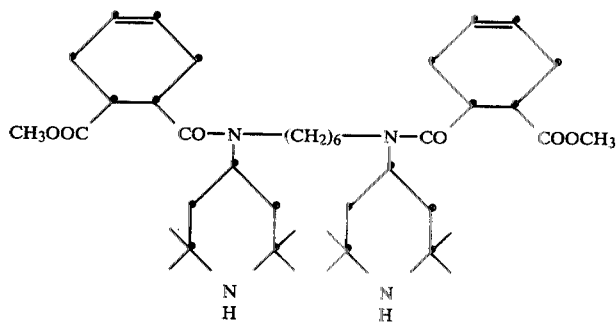 No. 30 melting point 124–131°

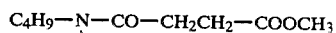 No. 31
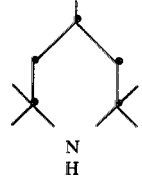

oil, boiling point 175°/0.1 mm Hg

EXAMPLE 7

100 g of finely powdered potassium carbonate are added to a suspension of 187 g (0.3 mol) of dimethyl ester No. 26 in 900 ml of 2-butanone. 79.2 g (0.63 mol) of dimethyl sulfate are then added dropwise at room temperature in the course of 1 hour, with stirring and slight ice-cooling, and during this addition the temperature rises to about 27°. The reaction mixture is now refluxed for a further 20 hours and cooled and the resulting white suspension is filtered. The filtrate is evaporated under a waterpump vacuum, the residue is dissolved in 2 liters of hot cyclohexane and the solution is stirred briefly with 30 g of silica gel 60 (Merck) and with the addition of kieselguhr, is clarified by filtering the hot solution. On cooling the filtrate, compound No. 32 is made to crystallise and the crystals are filtered off and dried. Melting point 118°–120°.

$C_{36}H_{66}N_4O_6$ Calculated: C, 66.42; H, 10.22; N, 8.61%. (650.91) Found: C, 66.5; H, 9.9; N, 8.5%.

CH₃OOC—CH₂CH₂—CO—N—(CH₂)₆—N—CO—CH₂CH₂—COOCH₃  No. 32

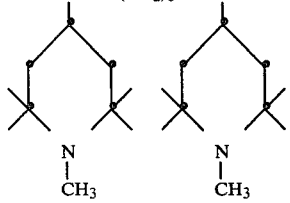

This compound has also been obtained in one step by reacting compound No. 10 with 4 mols of dimethyl sulfate (see Example 8).

Compound No. 33, which melts at 169°-170°, is obtained analogously by reaction with diethyl sulfate.

CH₃OOC—CH₂CH₂—CO—N—(CH₂)₆—N—CO—CH₂CH₂—COOCH₃  No. 33

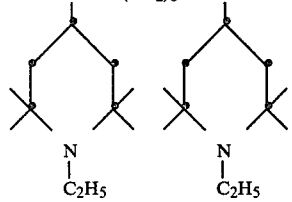

The analogous reaction of compounds Nos. 24 and 25 with 2 mol equivalents of dimethyl sulfate yields the compounds Nos. 34 and 35.

CH₃OOC—CH₂CH₂—CO—N—CH₂CH₂—COOOC₂H₅  No. 34

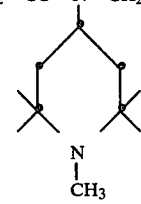

oil, boiling point 210°/0.01 mm Hg

CH₃
|
HO—CH—CH₂—N—CO—CH₂CH₂—COOCH₃  No. 35

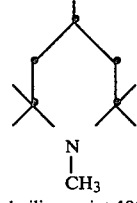

oil, boiling point 195°/0.05 mm Hg

EXAMPLE 8

165.8 g (1.2 mols) of finely powdered potassium carbonate are added to a suspension of 161.7 g (0.25 mol) of compound No. 23 in 600 ml of 2-butanone. 138.7 g (1.1 mols) of freshly distilled dimethyl sulfate are then added dropwise in the course of one hour at room temperature, with stirring and the mixture is then stirred at the reflux temperature for a further 24 hours. To isolate the product, the white suspension is cooled to room temperature and filtered, the salt residue is washed well with methylene chloride and the combined filtrates are evaporated under a waterpump vacuum. The residue is dissolved in 1,600 ml of n-hexane at the reflux temperature, 40 g of silica gel 60 (Merck) are added to the solution, which is not quite clear, and the mixture is kept at the reflux temperature for a further 15 minutes. The mixture is now filtered hot to remove the silica gel 60, the clear filtrate is concentrated and compound No. 36 is made to crystallise by cooling and is filtered off and dried in vacuo at 60°. A colourless crystalline powder of the geometric isomers is obtained which has a melting point of 141°-155°.

C₄₀H₇₀N₄O₆ Calculated: C, 68.36; H, 10.04; N, 7.97%. (703.02) Found: C, 68.6; H, 10.1; N, 8.2%.

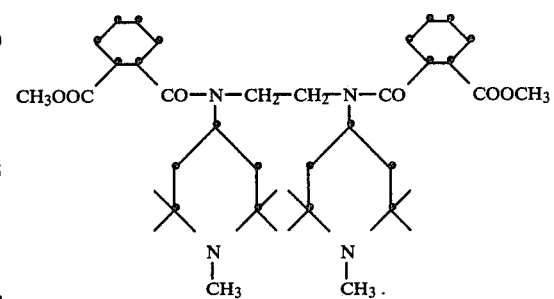

No. 36

Compound No. 37 is prepared analogously from compound No. 22 and excess dimethyl sulfate.

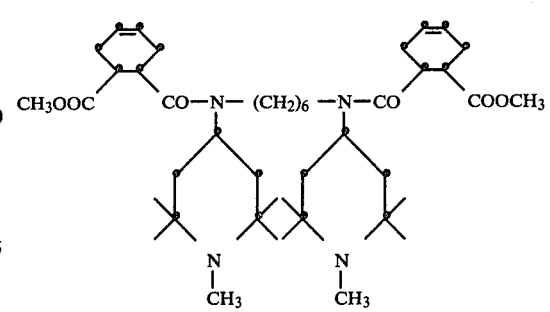

No. 37

EXAMPLE 9

A mixture of 208.2 g of compound No. 10, 250 g of allyl bromide, 250 g of potassium carbonate and 5 g of finely powdered potassium iodide in 500 ml of 2-butanone is refluxed for 48 hours, with stirring. The reaction mixture is then filtered while still warm, the filtrate is freed from the solvent and the excess allyl bromide under a waterpump vacuum and the residue is recrystallised from about 2 liters of n-hexane, the pure compound No. 38 with a melting point of 97°–98° being obtained.

$C_{44}H_{74}N_4O_6$ Calculated: C, 69.99; H, 9.88; N, 7.42%.
(755.1) Found: C, 70.1; H, 10.2; N, 7.5%.

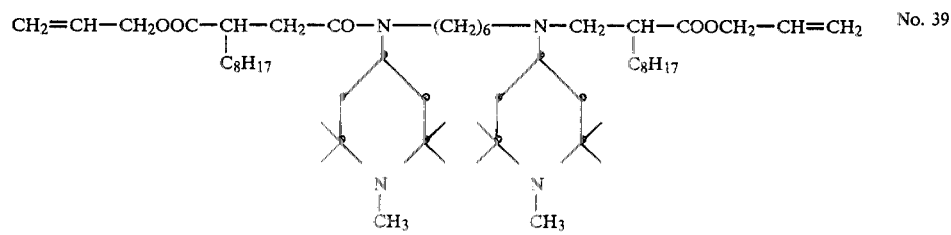

The allyl compounds Nos. 39, 40 and 41 are obtained analogously from compounds Nos. 8, 13 and 21.

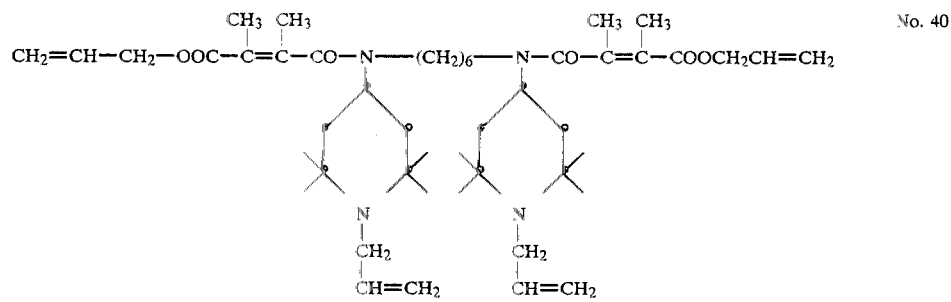

oil

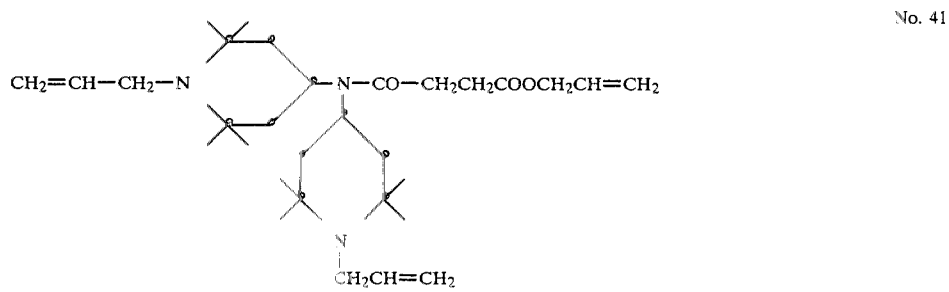

melting point 101–103°

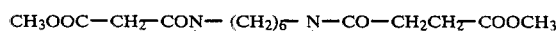

melting point 99–100°.

Compound No. 42 is obtained analogously from compound No. 26 and 2 mol equivalents of benzyl bromide.

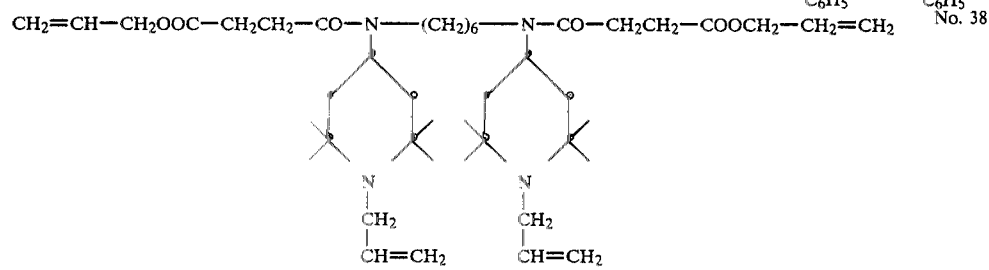

melting point 154–156°.

EXAMPLE 10

5 g of compound No. 26 in 15 g of acetic anhydride, with the addition of 2 drops of sulfuric acid, are heated at 90° for 48 hours. All of the acetic anhydride is then distilled off in vacuo and the residue is subjected to repeated recrystallisation from a little methylene chloride with the addition of diethyl ether, and the diacetyl compound No. 43 with a melting point of 130°–132° is obtained.

$C_{38}H_{66}N_4O_8$ Calculated: C, 64.56; H, 9.41; N, 7.93%. (706.93) Found: C, 64.3; H, 9.3; N, 7.9%.

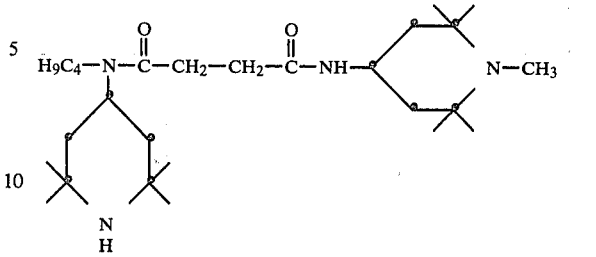

No. 45

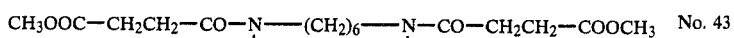 No. 43

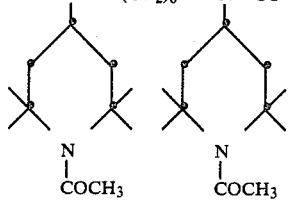

EXAMPLE 11

30 g of the amidocarboxylic acid No. 3 are reacted with 13 g of thionyl chloride in 150 ml of methanol, by a procedure analogous to that of Example 6, to give the methyl ester. The latter boils at 175°/0.1 mm Hg (bulb tube) (Compound No. 44). 0.16 g of sodium methoxide is added to a melt of 16.6 g (0.051 mol) of the methyl ester No. 44 and 10.2 g (0.06 mol) of 4-amino-1,2,2,6,6-pentamethyl-piperidine and the mixture is heated at 165°–170° in a gentle stream of $N_2$ for 24 hours, with stirring. For working up, the reaction mixture is dissolved in n-hexane, the solution is treated for 1 hour with 8 g of Tonsil AC and 10 g of silica gel 60 (Merck) and filtered and the filtrate is freed first from all of the solvent and then from excess 4-amino-1,2,2,6,6-pentamethylpiperidine, in vacuo. The crude diamide is then distilled under a high vacuum (bulb tube): boiling point 240°–245°/0.1 mm Hg.

$C_{27}H_{52}N_4O_2$ Calculated C, 69.78; H, 11.28; N, 12.06%. (464.71) Found: C, 69.5; H, 10.9; N, 12.2%.

Compound No. 46 is obtained analogously from the dimethyl ester No. 32 and excess N-hexyl-methylamine.

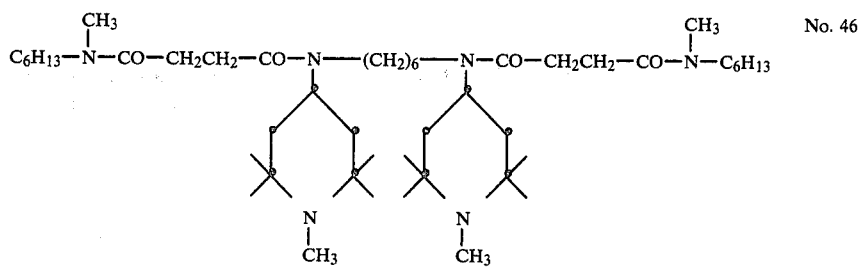 No. 46 melting point 60–62°

EXAMPLE 12

Preparation of Oligomeric Polyesters 19.53 g (0.03 mol) of dimethyl ester No. 32 together with 6.04 g (0.03 mol) of 1-(2-hydroxyethyl)-4-hydroxy-2,2,6,6-tetramethyl-piperidine and 0.2 ml of tetrabutyl orthotitanate (monomer) in 200 ml of anhydrous xylene, are heated slowly, in a gentle stream of nitrogen, to 140° C. in the course of about 3 hours, the methanol split off being distilled off continuously. The temperature is then kept at 145°–150° for a further 8 hours. The crude, oligomeric ester is cooled to 50° and dissolved in a little chloroform, the solution is filtered and the filtrate is then poured slowly, at room temperature, into 300 ml of acetonitrile, with vigorous stirring with a turbine stirrer, whereupon the polyester is precipitated. The acetonitrile is decanted off from the precipitate, the precipitate is redissolved in methylene chloride and the solvent is removed completely, first under a waterpump vacuum and then under a high vacuum, compound No. 47 being obtained in the form of a brittle solid. It sinters at about 95° and is completely melted at 140° and has an average molecular weight (vapour pressure osmometry) of about 17,000.

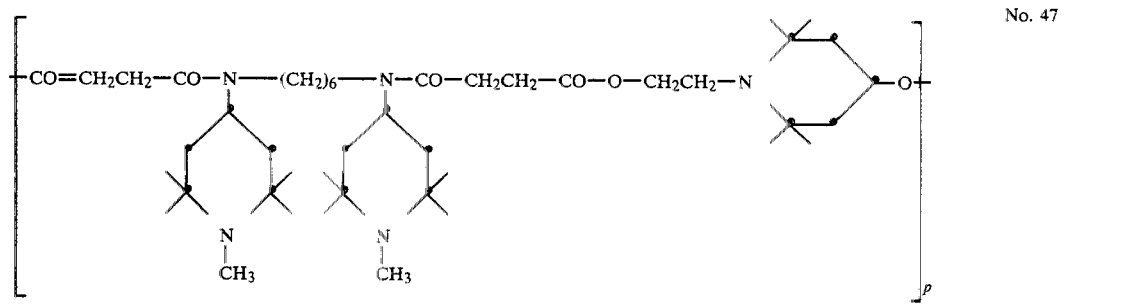

In an analogous manner, polyesters Nos. 48 and 49 are prepared from dimethyl ester No. 26, and polyester No. 50 is prepared from dimethyl ester No. 28.

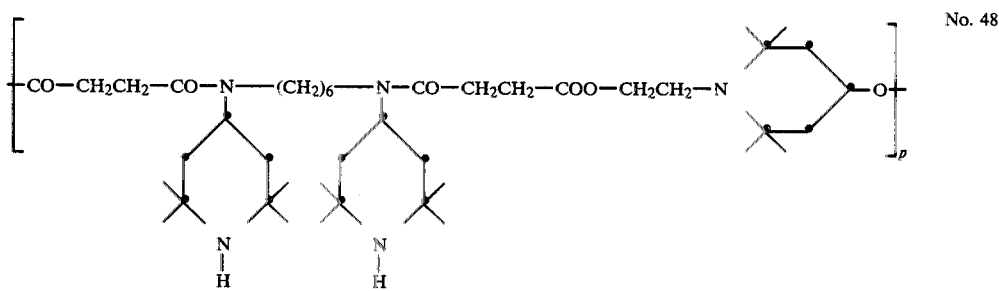

softening temperature above about 95°, $\overline{M}_n$ (osmometry) 6,900

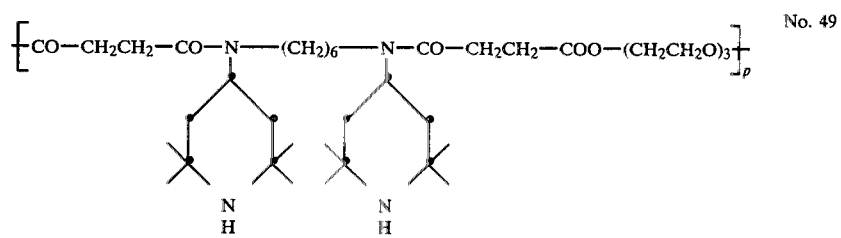

softening temperature above about 50°, $\overline{M}_n$ 5,300

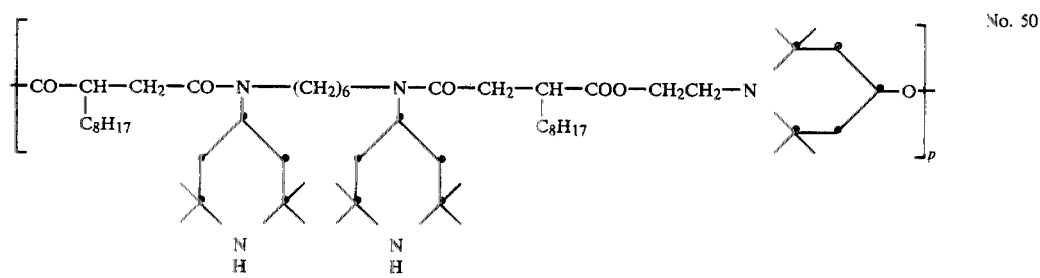

softens above about 60°, $\overline{M}_n$ 6,600

Analogously, polyester No. 51 is prepared from compound No. 27, polyester No. 52 is prepared from compound No. 36 and polyester No. 53 is prepared from compound No. 34.

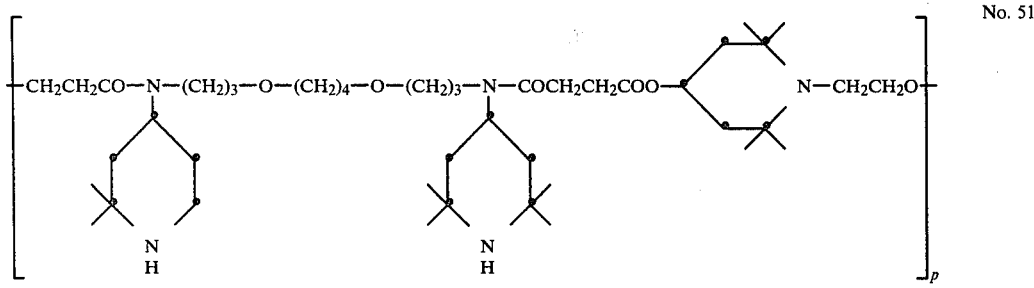

No. 51 softening temperature about 70°, $\overline{M}_n$ 7,100 softening temperature about 90°, $M_n$ 1,900

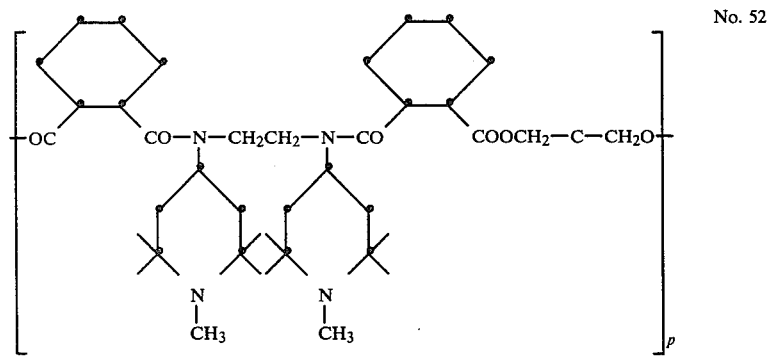

No. 52 softening temperature about 135°, $\overline{M}_n$ 2,270

When the procedure of Example 12 is repeated using

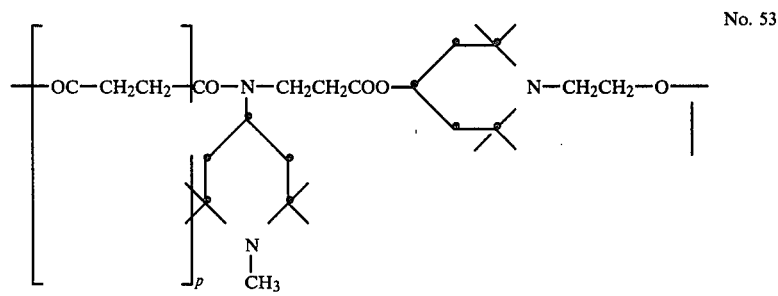

No. 53 softening temperature about 110°, $M_n$ 2,740

Polyester No. 54 is obtained by auto-condensation of compound No. 35 by the method given above.

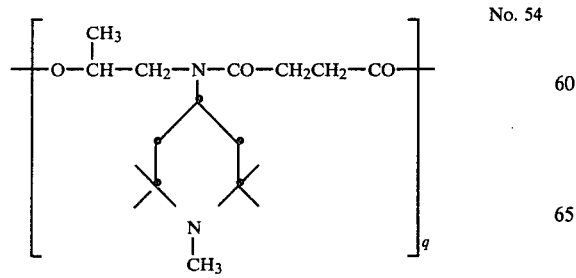

No. 54

0.1 g of lithium amide and 0.1 g of aluminium triisopropylate as the catalyst, in place of the tetrabutyl titanate, polyesters Nos. 55-60 are obtained from diallyl ester No. 38 and the corresponding diols

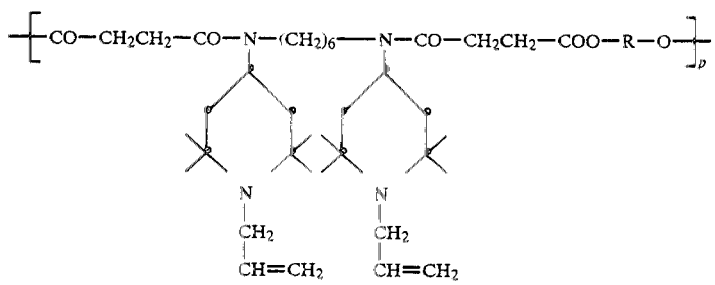

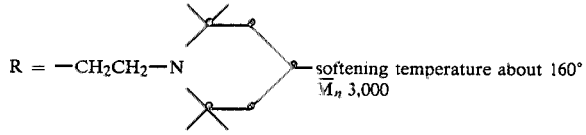 No. 55

R = —CH₂CH₂—N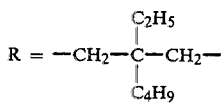 softening temperature about 160°
$\overline{M}_n$ 3,000

R = —CH₂CH₂—O—CH₂CH₂—O—CH₂CH₂— No. 56 softening temperature 55°, $\overline{M}_n$ 12,300

R = residue of "polyethylene glycol 300" No. 57 softening temperature about 20°, $\overline{M}_n$ 3,700

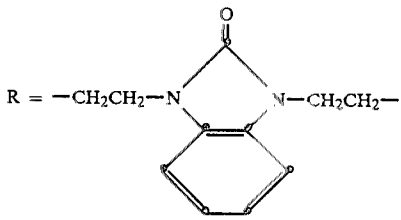 No. 58 softening temperature 75°, $\overline{M}_n$ 7,500

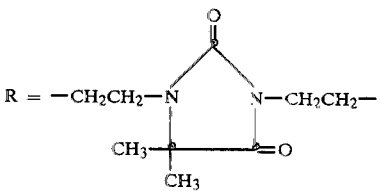 No 59 softening temperature 75°, $\overline{M}_n$ 6,300

R = —CH₂CH₂—N⟨...⟩N—CH₂CH₂— No. 60 softening temperature about 85°, $\overline{M}_n$ 6,800
melting point 130°

Polyesters Nos. 61-63 are obtained analogously from diallylester No. 39 and the corresponding diols.

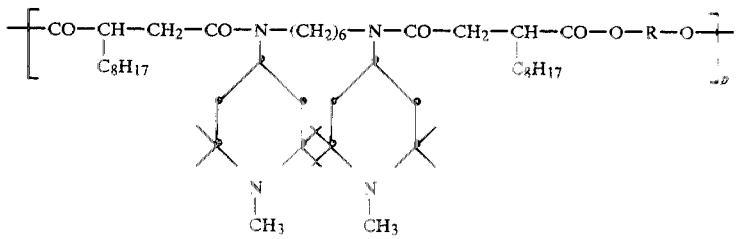

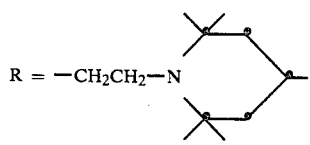

softening temperature about 50°, $\overline{M}_n$ 4,900

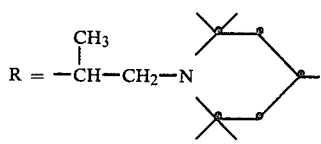

softening temperature about 65°, $\overline{M}_n$ 6,800

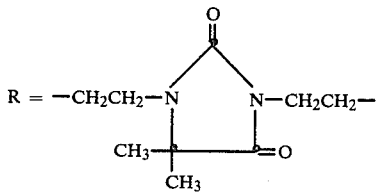

waxy compound, $\overline{M}_n$ 2,000

No. 61

No. 62

No. 63

EXAMPLE 13

Preparation of Oligomeric Polyamides 26.4 g (0.035 mol) of diallyl ester No. 38 and 4.1 g (0.035 mol) of 1,6-diaminohexane are heated to about 100°. 0.12 g of sodium methoxide and 0.18 g of aluminium isopropoxide are added, under a nitrogen atmosphere, to the resulting clear melt, with stirring. In a gentle stream of N₂, the temperature is gradually raised to 170°, allyl alcohol, distilling off slowly. After 20 hours at about 170°, the viscous melt is cooled to 50° and dissolved in chloroform, the solution is filtered through a layer of kieselguhr and the filtrate is concentrated to about 50 ml and poured slowly into 300 ml of acetonitrile at about 0°, with vigorous stirring with a turbine stirrer, whereupon the oligomeric amide is precipitated. The acetonitrile is decanted off, the precipitate is dissolved in methylene chloride and the solvent is removed, first under a waterpump vacuum and then, to completion, under a high vacuum, and by this means the solid, brittle compound No. 64 is obtained. It sinters at 80°, has melted completely at 100° and has an average molecular weight (vapour pressure osmometry) of about 2,300.

EXAMPLE 14

Reaction with Diglycidyl Ethers to give Oligomeric Polyethers 21.8 g (0.035 mol) of dimethyl ester No. 26, together with 11.9 g (0.035 mol) of bisphenol A diglycidyl ether and 0.17 g of dimethyl-benzylamine are heated slowly to a maximum temperature of 140°-143° in a N₂ atmosphere, with stirring, and the mixture is stirred for a further 8 hours at this temperature. For working up, the viscous melt is cooled and dissolved in methylene chloride, the solution is filtered through a layer of kieselguhr and the filtrate is concentrated to about 80 ml. This solution is now poured slowly, at room temperature, into 400 ml of a 1:1 mixture of acetonitrile and methanol, with vigorous stirring with a turbine stirrer, the polymeric compound being precipitated. The precipitate is separated off and redissolved in methylene chloride and the solvent is removed in vacuo and then, to completion, under a high vacuum, and by this means the oligomeric polyether No. 65 is obtained in the form of a brittle compound which can be pulverised easily. It sinters at about 105°, has melting at 135° and has an average molecular weight (vapour pressure osmometry) of about 19,000.

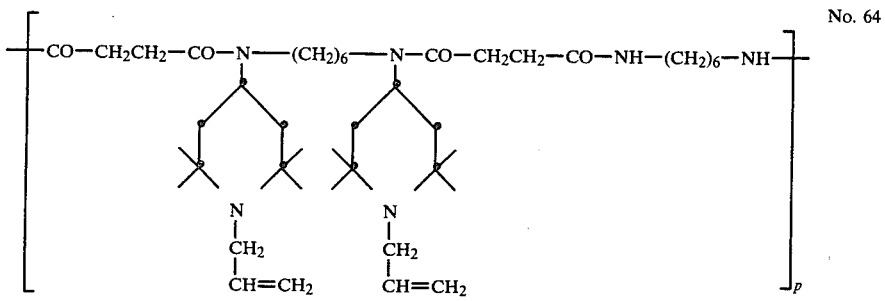

No. 64

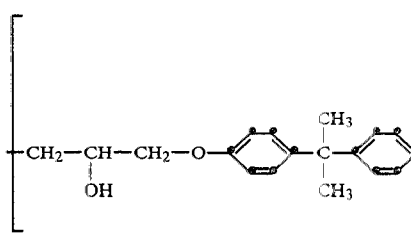 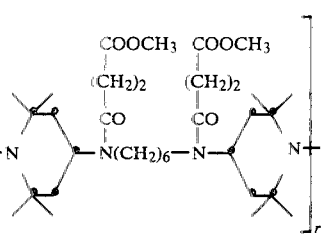

No. 65

EXAMPLE 15

Reaction with Dihalide to give Polyesters

A mixture of 22.93 g (0.025 mol) of compound No. 9 and 5.34 g of trans-1,4-dibromo-2-butene (0.025 mol), 8.28 g of powdered potassium carbonate and 0.2 g of finely powdered potassium iodide in 100 ml of 2-butanone are refluxed (80°) for 28 hours, with stirring. To isolate the oligomeric ester, the reaction mixture is clarified by filtration through a layer of Hyflo, the filtrate is freed from the solvent in vacuo and the residue is dissolved in about 50 ml of methylene chloride. This solution is allowed to run slowly into 700 ml of acetonitrile at room temperature, with vigorous stirring with a turbine stirrer (Polytron apparatus), and by this means the oligo-ester is precipitated as a resin. The supernatant acetonitrile is now decanted off, the resin which has precipitated is redissolved in a little methylene chloride and the precipitation procedure in acetonitrile as described above is repeated. The precipitated oligo-ester (No. 66) is dried in vacuo under 0.05 mm Hg, a colourless powder with a softening point of about 40° being obtained by this means. Mean molecular weight $M_n$: 4,000 (vapour pressure osmometer). Residual bromine content: <0.15%.

EXAMPLE 17

Stabilisation of Polypropylene against Light 100 parts of polypropylene powder (Moplen, fibre grade, from Montedison) are homogenised with 0.2 part of octadecyl β-(3,5-di-tert.-butyl-4-hydroxyphenyl)-propionate, 0.1 part of calcium stearate and 0.25 part of a stabiliser from Table 1 below, in a Brabender plastograph at 200° C. for 10 minutes. The composition thus obtained is removed from the kneader as rapidly as possible and pressed in a toggle press to give a 2-3 mm thick sheet. Part of the resulting blank is cut out and pressed between two high-gloss hard aluminium foils with a manual hydraulic laboratory press for 6 minutes at 260° to give a 0.1 mm thick film, which is immediately chilled in cold water. Sections are now punched from this film and exposed in a Xenotest 1200. These test pieces are removed from the exposure apparatus at regular intervals and tested in an IR spectrophotometer to determine their carbonyl content. The increase in the carbonyl extinction at 5.85 μm during exposure is a measure of the photo-oxidative degradation of the polymer (cf. L. Balaban et al., J. Polymer. Sci. Part C; 22, 1059–1071 (1969)) and experience has shown that it is associated with a deterioration in the mechanical prop-

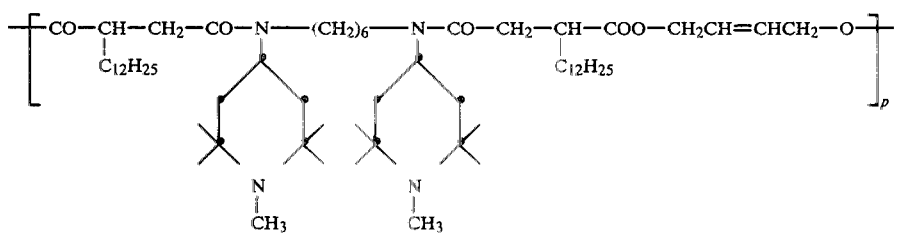

No. 66

EXAMPLE 16

Salt Formation

A solution of 42.4 g (0.1 mol) of compound No. 18 in 200 ml of methanol is neutralised with a solution of 18.8 g (0.1 mol) of p-toluenesulfonic acid in 100 ml of methanol, with stirring. The solution of the salt (compound No. 67) is evaporated and the pulverulent residue is dried under 0.1 mm Hg and at 50°. The salt softens at about 70° and has melted completely at 120°.

erties of the polymer. The time taken to reach a carbonyl extinction of about 0.3, at which the comparison film is brittle, is taken as a measure of the protective effect.

The ratio of this exposure time to the exposure time for a blank sample without light stabiliser is the protection factor PF.

$$PF = \frac{\text{exposure time for sample}}{\text{exposure time for blank sample}}$$

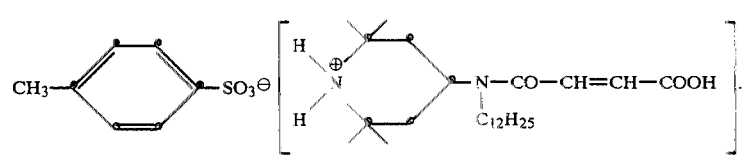

No. 67

Table 1 gives the protection factors for the light stabilisers of the formula I which were studied. Table 2 gives the corresponding values for oligomeric light stabilisers of the formula VII.

TABLE 1

| Light stabiliser | Exposure time | PF |
| --- | --- | --- |
| — | 760 hours | 1 |
| Compound No. 6 | 2,730 hours | 3.6 |
| 7 | 3,240 hours | 4.2 |
| 8 | 4,030 hours | 5.3 |
| 9 | 7,580 hours | 10.0 |
| 10 | 3,750 hours | 4.9 |
| 11 | 3,810 hours | 4.7 |
| 26 | 5,010 hours | 9.3 |
| 38 | 6,260 hours | 7.7 |
| 40 | 5,970 hours | 6.8 |

TABLE 2

| Light stabiliser | Exposure time | PF |
| --- | --- | --- |
| Compound No. 48 | 5,440 hours | 7.4 |
| 49 | 5,960 hours | 6.8 |
| 50 | 6,400 hours | 7.3 |
| 55 | 4,590 hours | 6.1 |
| 56 | 4,400 hours | 5.4 |
| 57 | 4,280 hours | 5.3 |
| 58 | 3,550 hours | 4.4 |
| 59 | 3,080 hours | 4.1 |
| 60 | 3,580 hours | 4.7 |
| 64 | 4,150 hours | 5.1 |

What is claimed is:

1. A compound of the formula I

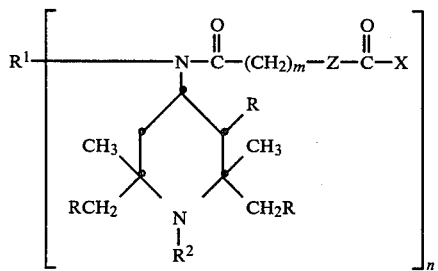

in which m is 0 or 1 and n is 1 or 2, X is —OH, —OR$^3$ or —N(R$^4$)(R$^5$), R is hydrogen or CH$_3$, R$^1$, if n is 1, is C$_1$-C$_{18}$-alkyl, C$_2$-C$_4$-hydroxyalkyl, C$_3$-C$_5$-methoxyalkyl, C$_5$-C$_8$-cycloalkyl, C$_6$-C$_7$-cycloalkylmethyl, unsubstituted C$_7$-C$_{12}$-aralkyl or C$_7$-C$_{12}$-aralkyl substituted by C$_1$-C$_4$-alkyl and/or hydroxyl, or phenyl, 2-cyanoethyl, 2-alkoxy(C$_1$-C$_4$)-carbonylethyl or a group of the formula II or III

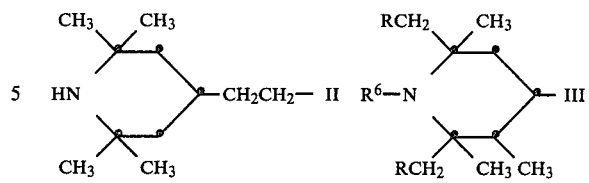

and if n is 2 is C$_2$-C$_{12}$-alkylene, C$_2$-C$_{12}$-alkylene interrupted by one or more —O— or —N(R$^7$)— or C$_6$-C$_{18}$-cycloalkylene, R$^2$ is hydrogen, an oxyl radical, C$_1$-C$_{12}$-alkyl, C$_2$-C$_4$-hydroxyalkyl, C$_3$-C$_5$-alkenyl, propargyl, benzyl or acetyl, Z is a group

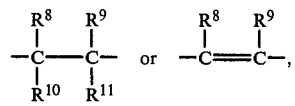

R$^3$ is C$_1$-C$_{12}$-alkyl, C$_2$-C$_4$-hydroxyalkyl, C$_3$-C$_{10}$-alkoxyalkyl, C$_3$-C$_5$-alkenyl, benzyl, cyclohexyl or a radical of the formula III, R$^4$ is hydrogen, C$_1$-C$_{12}$-alkyl, C$_3$-C$_5$-alkenyl, benzyl or cyclohexyl and R$^5$ is hydrogen, C$_1$-C$_{12}$-alkyl, allyl, C$_2$-C$_4$-hydroxyalkyl, cyclohexyl or a radical of the formula III, or R$^4$ and R$^5$ together with the N atom to which they are bonded form a pyrrolidine, piperidine, hexamethyleneimine or morpholine ring, R$^6$ is hydrogen or methyl, R$^7$ is methyl or one of the acyl radicals —CO—(CH$_2$)$_m$—Z—CO—X, R$^8$ is hydrogen or C$_1$-C$_{18}$-alkyl and R$^9$ is hydrogen, C$_1$-C$_{18}$-alkyl or C$_3$-C$_{12}$-alkenyl or phenyl, or R$^8$ and R$^9$ together with the two carbon atoms to which they are bonded form a saturated or unsaturated, at least 5-membered, carbocyclic ring, and R$^{10}$ and R$^{11}$ independently of one another are hydrogen or methyl, or a salt of such a compound with a mineral acid, sulfonic acid or organic phosphoric acid, or a salt of a compound of the formula I in which X is —OH with a monovalent to trivalent metal.

2. A compound according to claim 1, of the formula I, in which R is hydrogen.

3. A compound according to claim 1, of the formula I, in which n is 1 and R$^1$ is C$_2$-C$_{12}$-alkyl, or n is 2 and R$^1$ is C$_2$-C$_{12}$-alkylene, or C$_4$-C$_{10}$-alkylene interrupted by —O—.

4. A compound according to claim 1, of the formula I, in which R$^2$ is hydrogen, C$_1$-C$_4$-alkyl, allyl, benzyl or acetyl.

5. A compound according to claim 1, of the formula I, in which m is nought.

6. A compound according to claim 5, of the formula I, in which m is 0 and Z is a —CH=CH— or —CH$_2$—CH(R$^9$)— group, in which R$^9$ is hydrogen or alkyl, or Z is a 1,2-phenylene, 1,2-cyclohexylene or 1,2,3,6-tetrahydro-1,2-phenylene radical.

7. A compound according to claim 1, of the formula I, in which X is —OH or —OR$^3$ and R$^3$ is alkyl, allyl or benzyl.

* * * * *